US00PP22276P3

(12) United States Plant Patent
Seal

(10) Patent No.: US PP22,276 P3
(45) Date of Patent: Nov. 29, 2011

(54) KIWIFRUIT PLANT NAMED 'ZESH004'

(50) Latin Name: *Actinidia deliciosa×Actinidia chinensis*
Varietal Denomination: ZESH004

(75) Inventor: Alan Seal, Te Puke (NZ)

(73) Assignee: Zespri Group Limited, Mount Maunganui South (NZ)

( * ) Notice: Subject to any disclaimer, the term of this patent is extended or adjusted under 35 U.S.C. 154(b) by 0 days.

(21) Appl. No.: 12/660,392

(22) Filed: Feb. 24, 2010

(65) Prior Publication Data

US 2010/0333241 P1 Dec. 30, 2010

Related U.S. Application Data

(60) Provisional application No. 61/269,967, filed on Jun. 30, 2009.

(51) Int. Cl.
*A01H 5/00* (2006.01)

(52) U.S. Cl. ..... Plt./156

(58) Field of Classification Search ..... Plt./156
See application file for complete search history.

(56) References Cited

U.S. PATENT DOCUMENTS

PP11,065 P 9/1999 Lowe et al.
PP11,066 P 9/1999 Lowe et al.

*Primary Examiner* — June Hwu
(74) *Attorney, Agent, or Firm* — Knobbe Martens Olson & Bear, LLP

(57) ABSTRACT

A new and distinct kiwifruit variety is disclosed. The variety results from selection among a population of seedlings derived from crossing the kiwifruit selections known as 40-10-14e.92 (not patented, *Actinidia deliciosa*) and CK71_06 (not patented, *Actinidia chinensis*). The fruit of the plant of this new kiwifruit variety is characterized by early maturity, green flesh color, and a sweet, tropical/kiwifruit flavor. The new kiwifruit variety has been named 'ZESH004'.

5 Drawing Sheets

Latin name of the genus and species of the plant claimed: *Actinidia deliciosa×Actinidia chinensis.*

Variety denomination: 'ZESH004'.

BACKGROUND AND SUMMARY OF THE INVENTION

The invention relates to the discovery and asexual propagation of a new and distinct variety of kiwifruit, *Actinidia deliciosa×Actinidia chinensis* 'ZESH004', as herein described and illustrated. The new kiwifruit variety 'ZESH004' was selected from a population of seedlings derived from crossing two unpatented kiwifruit selections: *A. deliciosa* hexapoloid female 40-10-14e.92×*A. chinensis* diploid male CK71_06 in the course of a planned kiwifruit variety breeding program. The cross was made in November 2000 at Te Puke, Bay of Plenty, New Zealand. The new variety was selected as 16-01-03h.02 and has been named 'ZESH004'.

The new kiwifruit variety 'ZESH004' may be distinguished from presently available *Actinidia* cultivars by the following distinguishing characteristics:

The fruit of the new variety 'ZESH004' are high in sweetness (ripe brix) and vitamin C and are low in acidity compared with those of 'Tomua' (U.S. Plant Pat. No. 11,065).

The flesh of 'ZESH004' fruit are green in color at harvest but will change to a yellow-green color at warm temperatures, compared with 'Hayward' (non-patented ) and 'Tomua', which stay completely green regardless of storage temperature.

'ZESH004' are a cross between the *Actinidia deliciosa* and *Actinidia chinensis* species, compared with 'Hayward' and 'Tomua' which are *Actinidia deliciosa* species.

The fruit of the new kiwifruit variety 'ZESH004' mature earlier than those of 'Hayward'.

The fruit of the new kiwifruit variety 'ZESH004' are much sweeter than those of 'Hayward' and have a tropical flavor, as well as standard kiwifruit flavors.

The fruit shape at the stylar end of the new variety 'ZESH004' is blunt with a slight indentation compared with that of 'Hort16A' (U.S. Plant Pat. No. 11,066), which extends into a characteristic 'beak'.

The flesh of the new kiwifruit variety 'ZESH004' fruit is green-yellow in color when ripe for consumption, compared with 'Hayward' (non-patented) which is green in color.

'ZESH004' is tetraploid compared with 'Hayward' (non-patented) which is hexaploid.

'ZESH004' is tetraploid whereas its maternal parent (40-10-14e.92) is hexaploid, they can be distinguished by the fruit maturity timing, 40-10-14e92 is late maturing while 'ZESH004' is medium.

'ZESH004' is distinguished from its paternal parent (CK71 06—non-patented) as it is a female fruit bearing kiwifruit variety whereas CK71 06 is a male non-fruit baring kiwifruit.

Asexual propagation of the new kiwifruit variety 'ZESH004', at Te Puke, Bay of Plenty, New Zealand, by grafting shows that the unique combination of characteristics of the variety come true to form and are established and transmitted through succeeding propagation. In order to obtain true-to-type clones of the initial plant, asexually propagated plants were obtained by grafting dormant buds from the original seedling onto rootstocks.

BRIEF DESCRIPTION OF THE DRAWINGS

The accompanying photographs show typical specimens in full color of the fruit, flowers, and leaves of the new variety 'ZESH004', plants observed were three years old. The colors as depicted are as nearly true as is reasonably possible in a color representation of this type.

DETAILED DESCRIPTION OF THE PREFERRED EMBODIMENT

The following is a detailed description of the new variety. The specimens described were grown at Te Puke, Bay of Plenty, New Zealand. The observations were made on vines grafted onto existing *A. deliciosa* seedling rootstock, and managed under standard orchard practice. This included growing the plants on a standard pergola structure at a height of 1.8 m, and each plant was allowed to occupy a canopy area of approximately 15 $m^2$. The plants were three years old when described, and considered mature. Random measurements of each characteristic were obtained from samples of 6 plants.

Horticultural terminology is used in accordance with UPOV guidelines for kiwi. All dimensions are in millimeters and all weights are in grams (unless otherwise stated). Certain characteristics of this variety, such as growth and color, may change with changing environmental conditions (e.g., light, temperature, moisture), nutrient availability, rootstocks, or other factors. Color descriptions and other terminology are used in accordance with their ordinary dictionary descriptions, unless the context clearly indicates otherwise. Color names beginning with a capital letter designate values based upon The R.H.S. Colour Chart published by The Royal Horticultural Society, London, England.

PLANT AND FOLIAGE

The plant is a female plant that is tetraploid and expresses a spreading habit of medium vigor up until flowering, producing many long one-year-old canes. After flowering, vigor is reduced to low levels that require only light pruning.

Tomentose hairs are present on the young shoot at low density. Anthocyanin (red) coloration of the growing tip is absent or very weak on most shoots.

The mature one-year-old shoots of the plant are smooth and colored light yellowish-brown (R.H.S. 164 A and 164B) on the upper side. There are a moderate number of small to medium sized lenticels (2.3 mm average diameter), which are pale yellow-orange in color (R.H.S. 192B and 192C) and elliptical in shape. The size of the bud support is moderate and the leaf scar is moderate in size (similar to 'Hort16A'). Mature ones-year-old shoots average 12.9 mm in diameter between bud 5 and 6.

Figure 8:
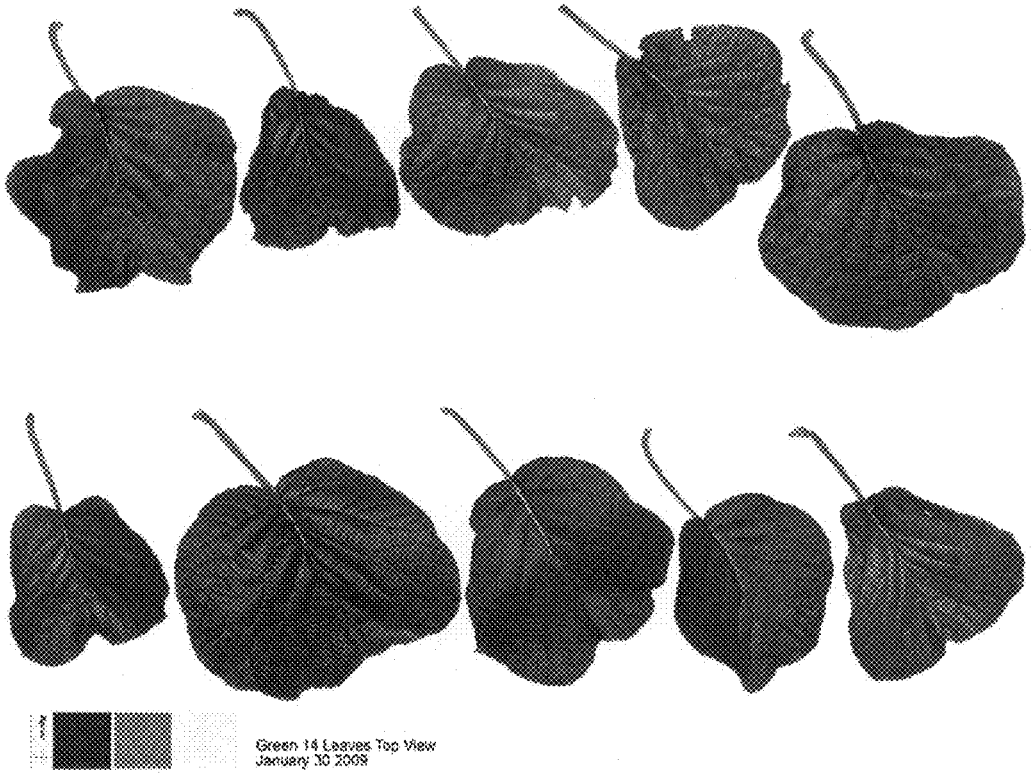
FIG. 8 shows mature leaves of the new kiwifruit variety 'ZESH004' from above (adaxial surface) (in the studio).
Figure 9:
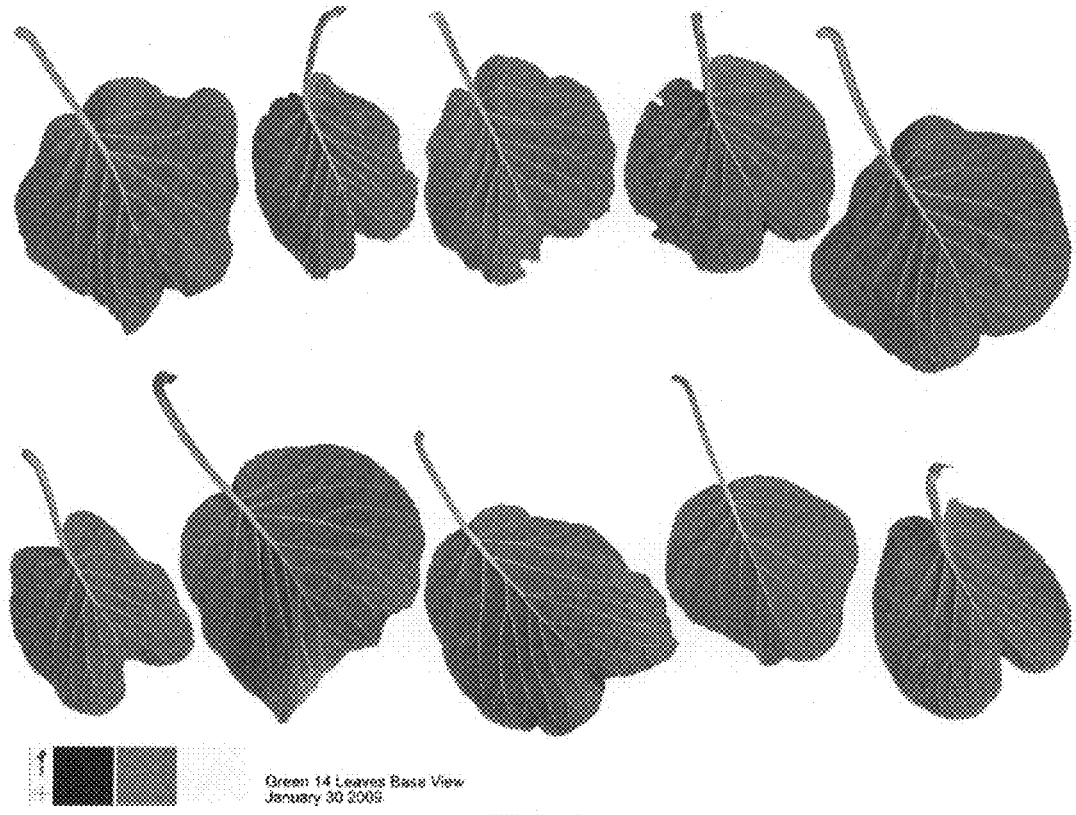
FIG. 9 shows mature leaves of the new kiwifruit variety 'ZESH004' from below (abaxial surface) (in the studio).

The leaf of 'ZESH004' is trapezoidal in shape with an emarginate shaped leaf tip (FIG. 8 and FIG. 9) and typically averages approximately 142 mm in length and 142 mm in width, the texture of the leaf is considered to be strongly rough. The leaf bases are touching. The color of the leaf blade is deep green (R.H.S. 139A) on the upper surface and greenish-yellow (R.H.S.148A) on the lower surface; with no variegation observed. Leaf petioles are approximately 72 mm long on average and have moderate anthocyanin coloration on the upper side of the petiole (R.H.S. 60C or 60D). Petioles have a moderate covering of short, firm hairs. On the underside of the leaf there are hairs on the sides of the veins, no spines have been observed.

INFLORESCENCE

The number of flowers in each inflorescence is most typically between one and two flowers, with each inflorescence comprising a single king flower that produce the largest fruit and up to two side flowers (0.33 per inflorescence on average) that produce smaller fruit. Each fruiting one-year-old shoot typically develops between one and six inflorescences, with an average of 3.5.

Flower pedicels average approximately 56 mm in length at mid-bloom.

Figure 5:
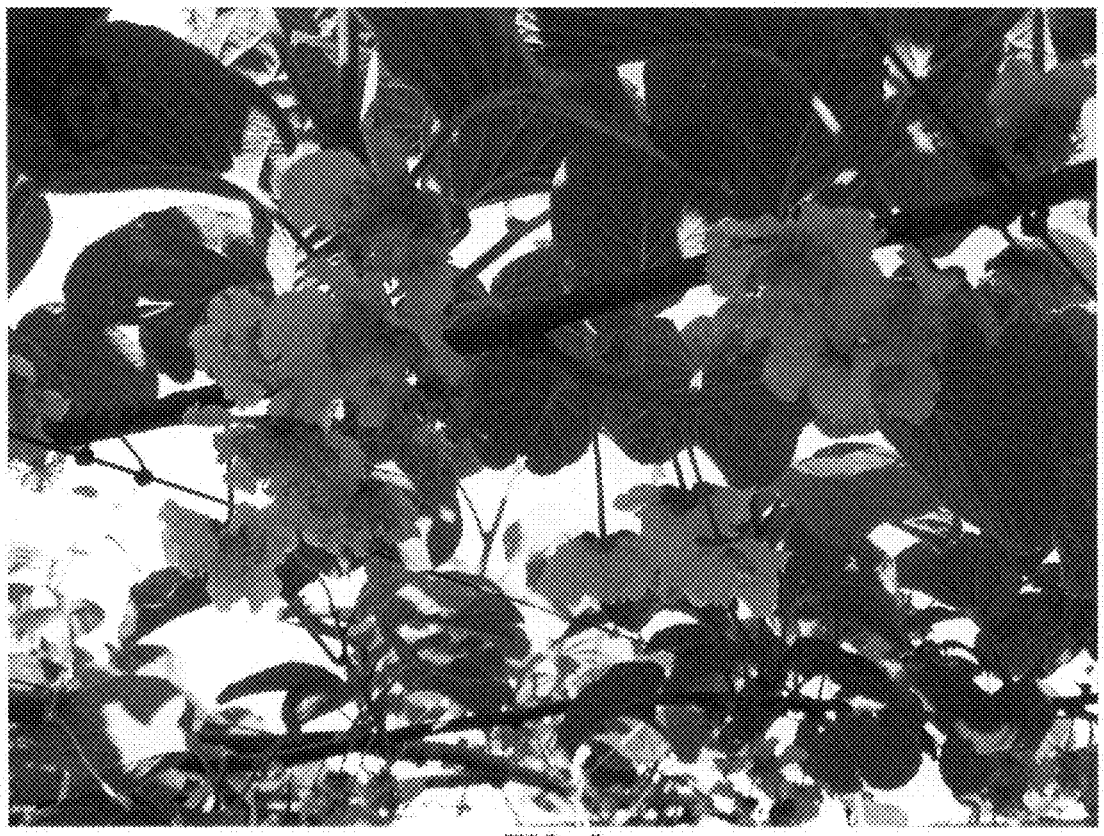
FIG. 5 shows the flowers of the new kiwifruit variety 'ZESH004' (on the vine).
Figure 6:
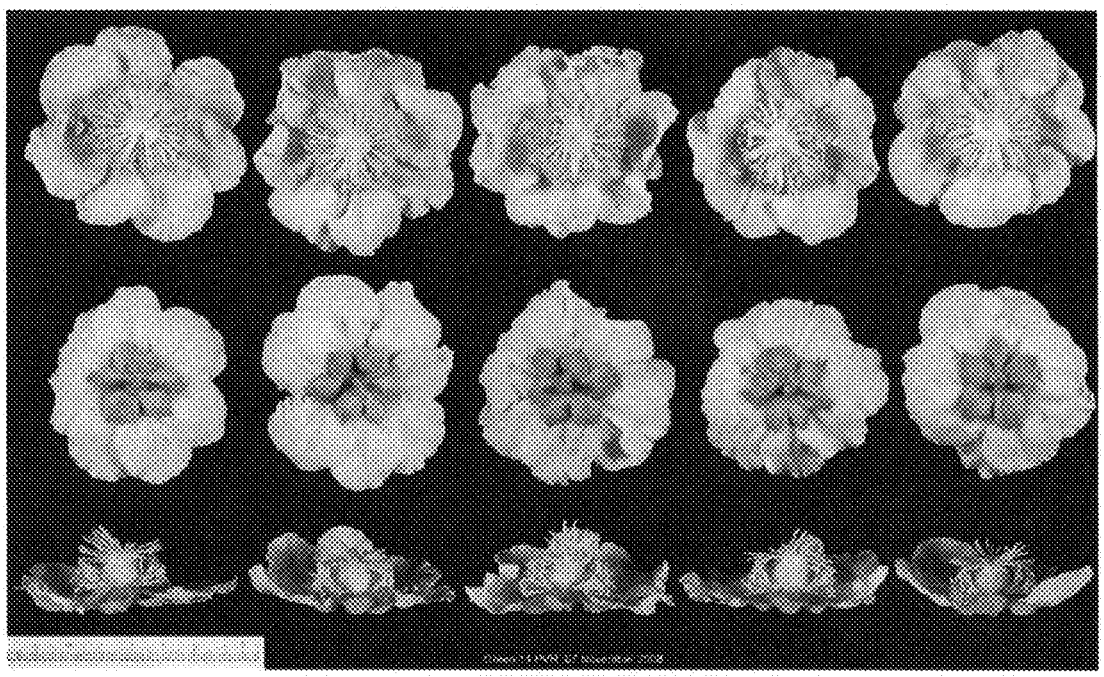
FIG. 6 shows the flowers of the new kiwifruit variety 'ZESH004' (in the studio).
Figure 7:
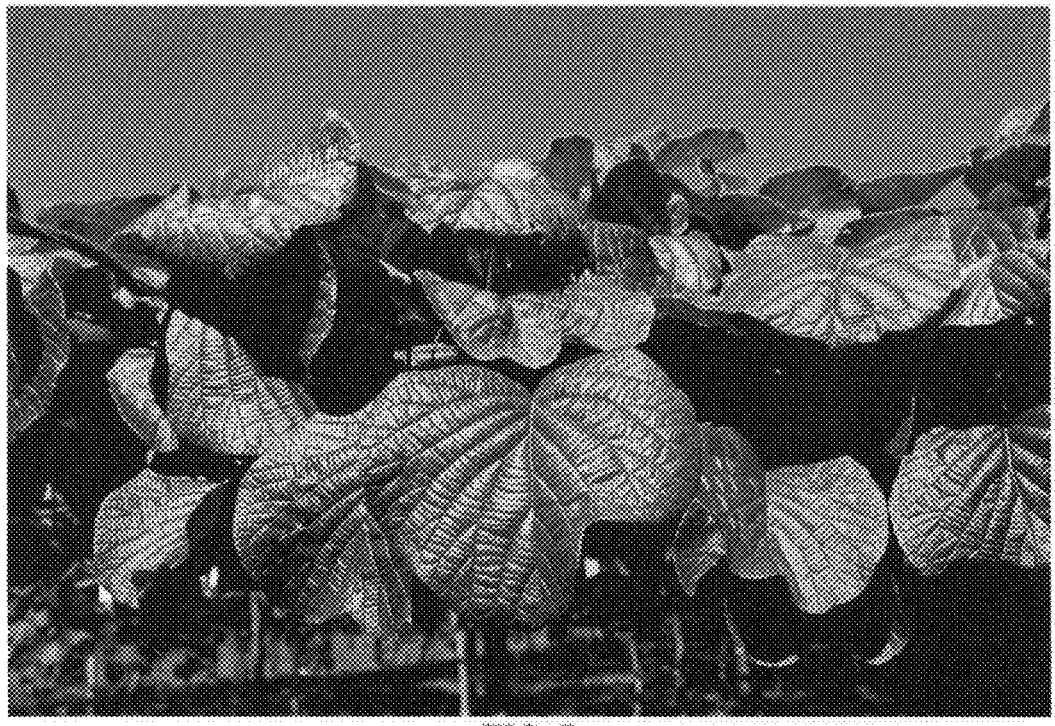
FIG. 7 shows mature leaves of the new kiwifruit variety 'ZESH004' (on the vine).

There are between five and 13 petals on each flower, with an average of 7.9. The petals are arranged overlapping and are white in color (R.H.S. 4C) when fully open, but with a light green base (R.H.S. 146A) (FIG. 5 and FIG. 6). Petals are involute in shape in cross-section and petals are slightly crimped. Flowers also contain between four and seven sepals (6.3 on average) that are mainly brown in color (R.H.S. 164C), but graduating into a green color (R.H.S. 145A) towards the ovary (FIG. 6). No obvious calyx ring has been observed. Each flower produces between 29 and 48 styles (40 on average) with a semi-erect attitude, that are 10.1 mm long on average, thick relative to other kiwifruit and white in color (R.H.S. 155D). There are an average of approximately 102 stamens per flowers with yellow anthers (R.H.S. 16A).

Ovaries of the king flower are covered in fine hairs that are white in color (R.H.S. 155D). Anthocyanin (red) coloration of the ovaries in cross-section is absent at mid-bloom. Ovaries of the king flower have a mean length of 9.5 mm and are ovoid in shape.

FRUIT

Figure 3:
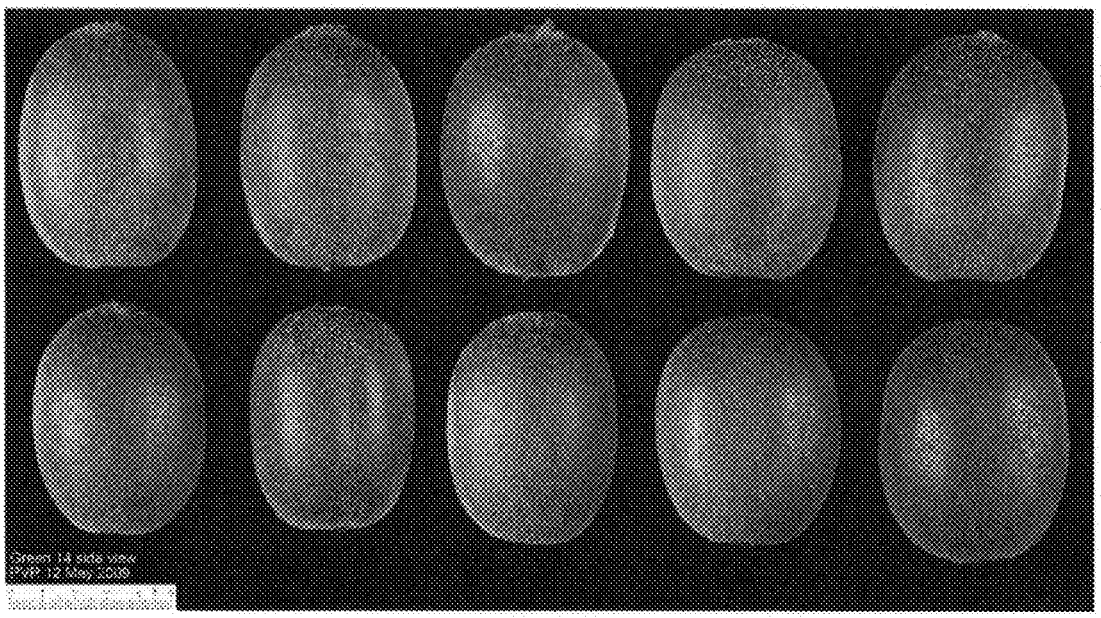
FIG. 3 shows typical fruit of the new kiwifruit variety 'ZESH004' (in the studio).

'ZESH004' fruit are moderate in size, approximately 116 g in weight on average when thinned to a crop load of 35 fruit per square meter of female canopy. The fruit dimensions average 65.4 mm in length, 56.2 mm maximum width, and 49.2 mm minimum width. The general fruit shape in longitudinal section is obovoid, with the general shape of the stylar end being flat, but with a slight indent (FIG. 3, FIG. 4) and the general shape at the stalk end being rounded. In cross-section, fruit shape at the median part of the fruit is ellipsoid.

Fruit stalks are long, averaging 63 mm long and 3.6 mm in diameter and are brown in color (R.H.S. 199A).

Soft light brown (R.H.S. 165B) hairs are present on the mature fruit. Fruit hairs are short (2-3 mm long) and occur at a moderate density. The skin of fruit is a green-brown in color (R.H.S. 191A) when fruit have been protected from direct sun exposure, but the skins changes to red-brown in color (R.H.S.

166A) on exposed fruit. The skin is covered with numerous lenticels that are light orange white in color (R.H.S. 164B) and are quite conspicuous. The combination of the green-brown skin and orange-white lenticels on the skins tends to result in the fruit appearing to be brown in color (R.H.S. 176D) when viewed from a distance of 30 cm or more.

Figure 4:
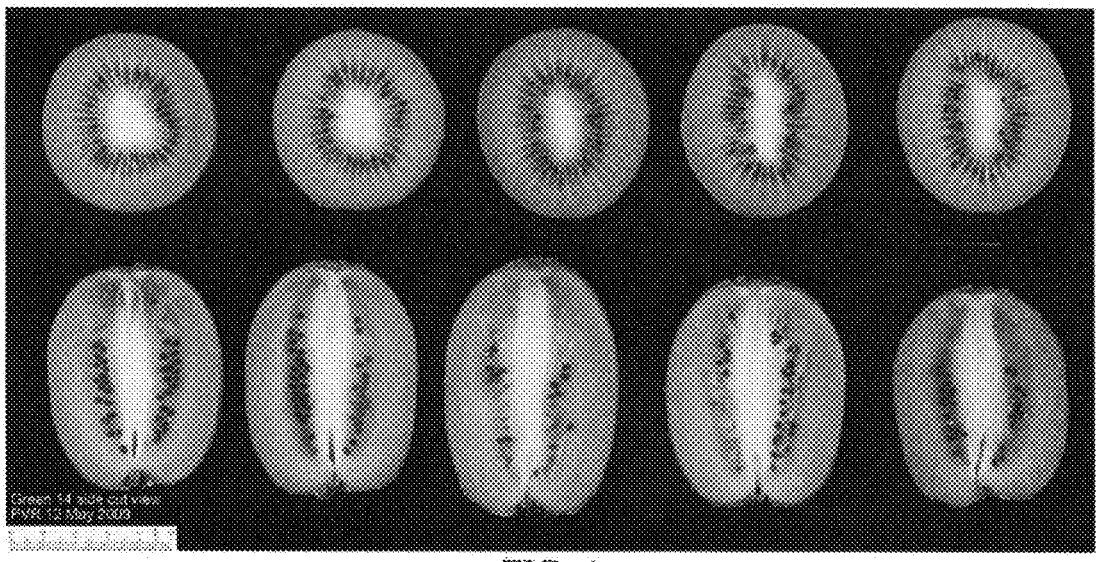
FIG. 4 shows the fruit of the new kiwifruit variety 'ZESH004' in longitudinal-section and cross-section (in the studio).

The outer pericarp is green in color (R.H.S. 146C) when the fruit are mature for harvest and at ripeness for eating. However, the outer pericarp will develop a light yellow-green color (R.H.S. 154A), if the fruit are maintained at warm temperatures of 20° C. after harvest or if they are left to ripen on the vines. The inner pericarp is light green in color (R.H.S. 146B) at maturity for consumption (FIG. 4). The core of the mature fruit is yellowish-white (R.H.S. 154D), ellipsoid in shape, and is approximately 16.8 mm in average diameter. Each fruit contains between 33 and 46 locules (38 on overage) and between 29 and 55 seeds can be counted on a transverse slice made through the middle of the fruit (43 on average).

The fruit are very sweet and slightly tangy with some tropical flavors, as well as having 'Hayward' kiwifruit flavors. Fruit can be ripened soon after they have been harvested in late March or early April in the Te Puke region of New Zealand using ethylene gas, or will soften during cold storage and become ripe for eating within 6 to 12 weeks at 1° C. The fruit average 20.3% soluble solids (measured as °Brix) and contain 149 mg of vitamin C and 1.33 g of titratable acidity (g citric acid equivalents) per 100 g of fresh weight at maturity for consumption.

CULTIVATION

'ZESH004' plants can be grown on the same rootstocks as other standard varieties such as 'Hayward' and 'Hort16A'. Rootstocks currently being used in New Zealand include *A. deliciosa* seedlings, *A. chinenis* seedlings, and 'Kaimai' (not patented).

Vegetative bud break occurs in early September in the Te Puke region of New Zealand, with flowering commencing in mid November, with a flowering period of approximately 14 days. In the Te Puke region of New Zealand, approximately 60% of the dormant 'winter' buds burst in spring and approximately 85% of these shoots will produce flowers. All flowers produced appear capable of setting a fruit that will survive to harvest, if they are pollinated. The fruit attain maturity for harvest according to the criteria of reaching 8% soluble solids in early April in the Te Puke region of New Zealand. Leaves persist on the plants until early winter (June to July) in the Te Puke region of New Zealand.

Figure 1:
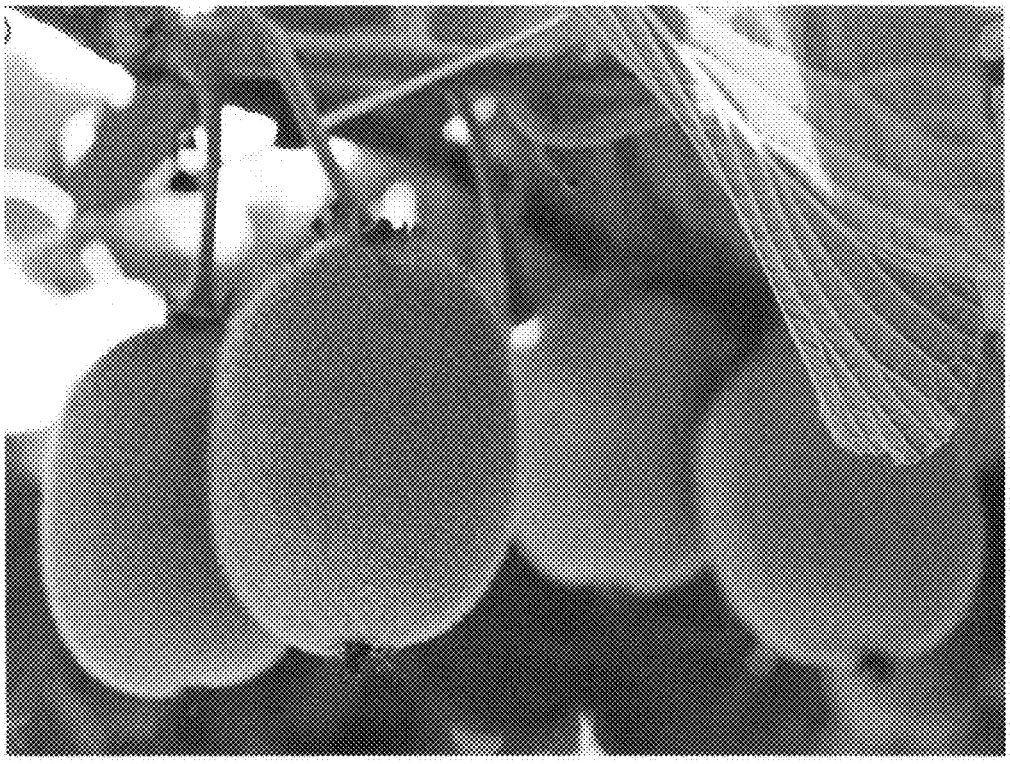
FIG. 1 shows typical fruit of the new kiwifruit variety 'ZESH004' (on the vine).
Figure 2:
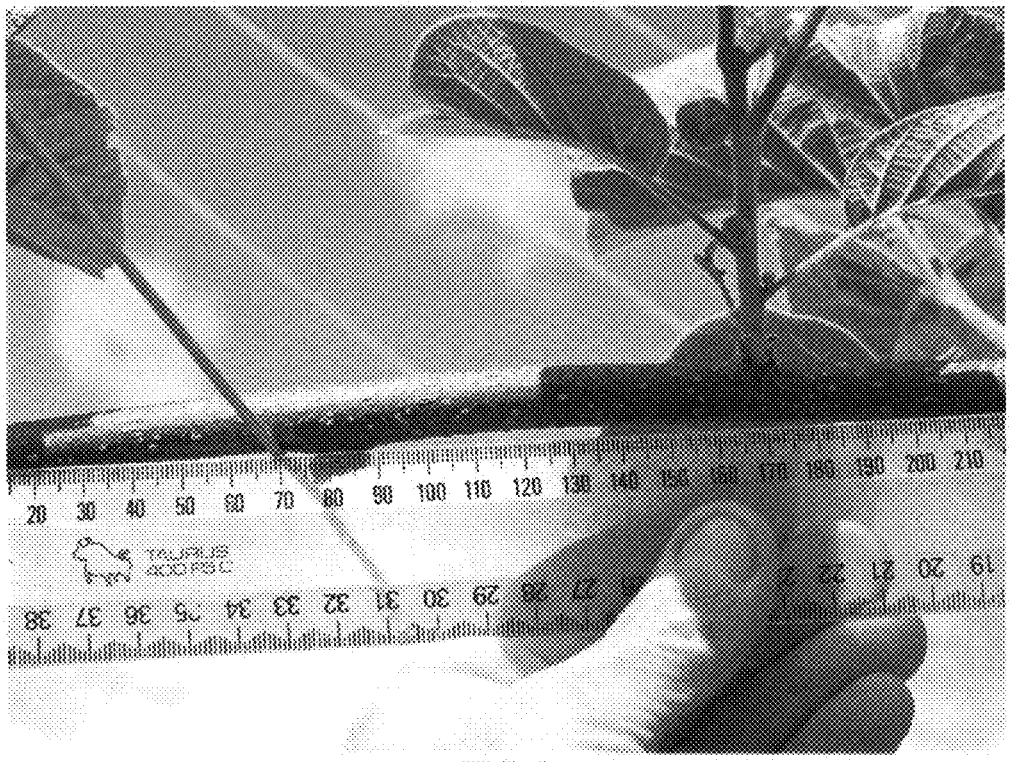
FIG. 2 shows typical one-year-old shoots (canes) of the new kiwifruit variety 'ZESH004' (on the vine).

In the absence of bud break enhancing chemicals, plants produce low to moderate flower numbers, with an average of 17 king flowers per meter of one-year-old cane in the Te Puke region of New Zealand. In non-thinned vines this would result in crop loads of 51 fruit per square meter of female canopy at standard cane spacings (FIG. 1). Fruit size is moderate (116 g) when thinned to a crop load of 35 fruit per square meter of female canopy and this would result in moderate yields of fruit.

Dormant canes of 'ZESY002' appear to be susceptible to Latania scale (*Hemiberlesia lataniae*) and leaves appear to be susceptible to brown headed leafroller (*Ctenopseustis obliquana*). There is also some evidence to suggest that fruitlets may have an increased susceptibility to *Sclerotinia sclerotiorum* infection when compared with 'Hayward' (non-patented). No other hose susceptibility testing has been completed at this stage.

Observations to date suggest that 'ZESY002' plants have a similar plant hardiness zone to 'Hort16A' (U.S. Plant Pat. No. 11,066) or 'Hayward' (non-patented) plants.

In post harvest storage, softening of harvested 'ZESH004' fruit can be delayed by placing fruit into cold storage. In this case, fruit can be successfully stored for between 12 and 16 weeks while maintaining average flesh firmness greater than one kgf. Once removed from long term cold store and returned to ambient temperatures, fruit continue to soften but can be held at 20° C. for one week for consumption.

We claim:

1. A new and distinct kiwifruit plant substantially as herein described and illustrated, characterized by fruit with a moderate-large fruit size, high natural yield potential, ovoid shape, yellow flesh color and potential for long storage.

* * * * *